United States Patent [19]

Kojima et al.

[11] 4,302,357
[45] Nov. 24, 1981

[54] CATALYST FOR PRODUCTION OF ETHYLENE FROM ETHANOL

[75] Inventors: Mitsuo Kojima; Takahiro Aida, both of Niitsu; Yukio Asami, Yokohama, all of Japan

[73] Assignee: Nikki Chemical Co., Ltd., Tokyo, Japan

[21] Appl. No.: 142,910

[22] Filed: Apr. 23, 1980

[30] Foreign Application Priority Data

May 31, 1979 [JP] Japan .................................. 54-68362

[51] Int. Cl.$^3$ .......................... B01J 21/04; B01J 27/18
[52] U.S. Cl. ........................................ 252/437; 252/436
[58] Field of Search ............... 252/437, 463, 628, 436; 585/640

[56] References Cited

U.S. PATENT DOCUMENTS 1,913,938  6/1933  Metzger et al. ...................... 585/640
3,249,557  5/1966  Oleck .................................... 252/463
3,637,406  1/1972  Bailey ............................. 423/628 X
4,207,424  6/1980  Winnick .............................. 585/640

FOREIGN PATENT DOCUMENTS 457938  7/1949  Canada ................................ 585/640

Primary Examiner—W. J. Shine
Attorney, Agent, or Firm—Blanchard, Flynn, Thiel, Boutell & Tanis

[57] ABSTRACT

An activated alumina catalyst containing alkali metal, sulfur, iron and silicon in an amount of 0.05 wt. % or less respectively, calculated as $Na_2O$, $SO_3$, $Fe_2O_3$ and $SiO_2$ and having a purity of 99.6 wt. % or more exhibits superior activity and selectivity when used in the dehydration reaction of ethanol to ethylene. By adding to the above mentioned high purity activated alumina catalyst a phosphate of one member selected from the metals of Group IIa, Group IIb, Group IIIa and Group IVb of the Periodic Table in an amount of from 0.05 to 5 wt. % of said catalyst there can be obtained a catalyst having more improved activity and selectivity as well as more increased mechanical strength.

8 Claims, No Drawings

CATALYST FOR PRODUCTION OF ETHYLENE FROM ETHANOL

BACKGROUND OF THE INVENTION

The present invention relates to an improved activated alumina catalyst having high activity and selectivity for prolonged periods of time when employed in a process for the production of ethylene from ethanol through a dehydration reaction.

For effecting the catalytic dehydration of ethanol in the vapor phase there have hitherto been utilized, as catalyst, silica-alumina, activated alumina, solid phoshoric acid, metal sulfate, etc. These catalysts, however, are observed to be defective in that the activity thereof is significantly decreased by the deposition of carbonaceous material on the surface of the catalyst during the course of the reaction, a satisfactorily high ethylene yield can not be obtained because ether, aldehyde, $C_4$-olefins, etc. are easily by-produced and so forth. In order to eliminate these defects there have been considered such counterplans that the reaction is operated at a high space velocity thereby suppressing the conversion rate of ethanol to a low degree, and the partial pressure of ethanol is decreased by the use of diluent gas.

We have devoted ourselves to investigations to develop a catalyst capable of eliminating the above mentioned defects inherent in conventional catalysts and exhibiting high efficiency as well as stability in the formation of the final product ethylene. Consequently, we have discovered the facts that a high purity alumina catalyst containing extremely reduced amounts of the remaining alkali metal, sulfur, iron and silicon components can exhibit high activity and high selectivity in the formation of ethylene and that the addition of a small amount of a certain kind of metal phosphate to said alumina can impart a high stability in addition to the aforesaid high activity and high selectivity. Through these processes of investigations, we have succeeded in developing an activated alumina catalyst capable of totally removing the defects inherent in conventional catalysts and thus completed the present invention.

SUMMARY OF THE INVENTION

According to the present invention the catalyst suitably employed in the production of ethylene from ethanol through dehydration comprises an activated alumina containing alkali metal, sulfur, iron and silicon in an amount of 0.05 wt. % or less respectively, calculated as $Na_2O$, $SO_3$, $Fe_2O_3$ and $SiO_2$ and having a purity of 99.6 wt. % or more. The high purity activated alumina catalyst according to the present invention can contain a phosphate of one member selected from the metals of Group IIa, Group IIb, Group IIIa and Group IVb of the Periodic Table in an amount ranging from 0.05 to 5 wt. % based on the weight of said high purity activated alumina.

DETAILED DESCRIPTION OF THE INVENTION

The first preferred feature of the catalyst according to the present invention consists in the components and properties of the activated alumina used therein. As is evident from the examples and comparative examples referred to hereinafter, the components and properties of the alumina bring about conspicuous differences on the catalyst performances such as activity (the conversion of ethanol) and selectivity (the yield of ethylene). It has been discovered that these differences are widely influenced by the contents of alkali metal, sulfur, iron and silicon and so forth. The amounts of said impurities contained in alumina, although the lower the better, should be 0.05 wt. % or less respectively. Such a high purity alumina preferably should be prepared from the materials such as metallic aluminum or organic aluminum salt, etc., but it is to be noted that alumina prepared by a different way may of course be employed. The other properties, for instance, such as specific surface area, pore volume, etc. are important, but it is the purity of the alumina that mainly exerts an influence on the amount of ethylene yield and accordingly the other factors should be said to be secondary. Therefore, if normal values be maintained, for instance, the specific surface area is maintained in the range of from 100 to 350 $m^2/g$ and the pore volume is in the range of from 0.15 to 0.50 cc/g or so, there will not be caused any special problem.

Next, the second preferred feature of the catalyst according to the present invention consists in that a small amount of a specific metal phosphate is added to the main catalytic component, namely alumina. As the metal phosphates suitably used in the present invention there can be enumerated those of magnesium, calcium, zinc, aluminum, zirconium, etc. belonging to Group IIa, Group IIb, Group IIIa and Group IVb of the Periodic Table, in particular phosphates of magnesium, calcium, zinc, etc. belonging to Group IIa and Group IIb of the Periodic Table. And, these metal phosphates are added to alumina in the amounts in the range of from 0.05 to 5.0 wt. %, preferably in the range of from 0.1 to 1.0 wt. %, based on the weight of said high purity alumina. With reference to the nature of above mentioned metal phosphates, viewed from the standpoint of activity, it is not specifically limited, in other words it may be an acid phosphate or a normal phosphate, but viewed from the standpoint of the moldability, in particular mechanical strength of the catalyst, the acid phosphate is more preferable.

The phosphate-containing catalyst according to the present invention can be prepared with ease through any one of the hitherto known methods, such as the thermal cracking method, precipitation method, sedimentation method, kneading method or joint use of them. As the raw material for preparing the alumina, the primary catalytic component, there can be employed nitrate, acetate, alkoxide, sulfate, chloride, alkali aluminate, alum, etc. which are capable of producing alumina or alumina hydrate when subjected to heat-treatment or hydrolysis. The alkali suitably used for hydrolysis includes caustic alkali, alkali carbonate, aqueous ammonia, ammonium carbonate, etc., preferably an alkali metal-free one. As the promoter components, for instance, the respective phosphates of magnesium, calcium, zinc, etc., there may be utilized commercially available high purity ones as they are, but it is more preferable to use one prepared by the conventional precipitation method which comprises adding to an aqueous solution of their nitrate, sulfate or acetate, an aqueous solution of normal ammonium phosphate, ammonium hydrogen phosphate, normal alkali phosphate, alkali hydrogen phosphate or the like. The method suitably utilized in the addition of each of said phosphates to the alumina component includes the sedimentation method or kneading method and even the dry mixing method.

The catalyst according to the present invention is applicable to any one of the fixed bed system, moving bed system and fluidized bed system, in other words, the application thereof is not specifically limited. As the method for molding the catalyst according to the present invention, there can be employed, depending on the purpose, an optional one selected from among the conventional tabletting method, extruding method, granulating method, etc., but in any case, a binder for use in tabletting or granulating should scarcely contain an alkali metal, sulfur, iron or silicon. The molded catalyst suitably used in the present invention may have a particle diameter ranging from 1.5 to 10 mm$\phi$ or so, but the particle diameter in practice is decided taking the pressure drop across the reactor into consideration.

In the preparation of ethylene from ethanol using the catalyst according to the present invention it is necessary that the catalyst bed should be maintained at a temperature of at least 300° C. or more or 450° C. or less. When operated at a temperature below the above specified temperature, it consequently decreases the ethylene yield because of the formation of ether, while, when operated at a temperature above said temperature, the formation of aldehyde or olefins becomes conspicuous as well as the formation of carbonaceous materials on the catalyst, which thereby shorten the catalyst's life. The liquid hourly space velocity (LHSV) of ethanol may be decided, depending on the catalytic activity, to be in the range of from 0.25 to 5.0 hour$^{-1}$, preferably in the range of from 0.5 to 3.0 hour$^{-1}$. The reaction may be conducted either at the ordinary pressure or at the increased pressure, preferably at a pressure in the range of from atmospheric pressure to 20 Kg/cm$^2$ G. The vapor of ethanol is generally supplied together with an inert gas such as steam and/or nitrogen, but in the case where the catalyst according to the present invention is employed, it can be operated or handled even when the vapor of ethanol alone is supplied. This is because the catalyst according to the present invention is characterized in that it does scarcely cause the side reactions and consequently the presence of carbonaceous deposits on the surface of the catalyst decreases.

DESCRIPTION OF THE PREFERRED EMBODIMENTS

EXAMPLE 1

500 ml of aqueous sodium aluminate solution was prepared by dissolving 52.4 g of sodium aluminate in water. 18.9 g of sodium citrate (dihydrate) was then added to the resulting aqueous solution and dissolved completely. Subsequently, the same was maintained at 50° C., and a 7 N nitric acid solution was dropped therein with stirring. Dropping was continued until the pH comes up to 7. Thereafter, the same was filtered, washed and dried as usual to thereby prepare an alumina (Catalyst A). This alumina was pelleted into cylindrical tablets being 3 mm in height as well as diameter. These tablets were subjected to 3 hours' calcination at 600° C. into catalysts. These catalysts were charged up to 60 ml in a 304 stainless steel tube reactor having an inside diameter of about 14 mm. It was placed at an elevated temperature of 370° C. and then ethanol was supplied thereto at a liquid hourly space velocity of 1.0 hour$^{-1}$ by means of a micropump. An activity test was performed on the catalyst while maintaining the pressure in the reaction zone at 10 Kg/cm$^2$ G. The obtained results are as shown in Table-1.

Comparative Examples 1 through 3

Various kinds of commercially available aluminas (Catalysts B, C and D) were pelleted and calcined according to the same procedure as Example 1 to thereby obtain catalysts respectively. The catalysts thus obtained were subjected to activity tests under entirely the same reaction conditions as Example 1. The obtained results are as shown in Table-1.

TABLE-1

| | Catalyst | Specific surface area* (m$^2$/g) | Pore volume (cc/g) | Mechanical strength (Kg/pellet) | Content of impurity (wt. %) | | | | Conversion of ethanol (mole %) | Yield of ethylene (mole %)** |
|---|---|---|---|---|---|---|---|---|---|---|
| | | | | | Na$_2$O | SO$_3$ | Fe$_2$O$_3$ | SiO$_2$ | | |
| Example 1 | A | 167 | 0.38 | 25.9 | 0.04 | trace | 0.002 | 0.03 | 94 | 90 |
| Comparative Example 1 | B | 328 | 0.40 | 27.5 | 0.02 | 0.42 | 0.04 | 0.04 | 90 | 85 |
| Comparative Example 2 | C | 225 | 0.20 | 31.5 | 0.04 | 2.49 | 0.80 | 0.41 | 95 | 65 |
| Comparative Example 3 | D | 280 | 0.32 | 27.4 | 0.35 | trace | 0.02 | 0.02 | 75 | 70 |

*Value measured according to BET method
**Value after the lapse of 100 hours from the start of reaction Conversion of ethanol (mole%) = $\frac{\text{Moles of the reaction products}}{\text{Moles of ethanol supplied}} \times 100$ Yield of ethylene (mole %) = $\frac{\text{Moles of ethylene produced}}{\text{Moles of ethanol supplied}} \times 100$ According to the results as shown in Table-1, it is a high purity alumina catalyst A containing little impurities that exhibits high conversion of ethanol as well as high yield of ethylene. In other words, of the impurities, the presence of alkali metal exceedingly decreases the conversion of ethanol and the presence of sulfur, iron or silicon exceedingly decreases the yield of ethylene respectively.

Comparative Examples 4 through 6

A molded alumina (Catalyst E) obtained by adding 1.1 wt. % of H$_2$SO$_4$ to Catalyst A according to Example 1, a commercially available molded silica-alumina (13% Al$_2$O$_3$; N631L manufactured by Nikki Chemical Co., Ltd.) and a molded silica-alumina (Catalyst F) obtained by adding 7.1 wt. % of Fe$_2$O$_3$ to said N631L were subjected to 3 hours' calcination at 600° C. into catalysts respectively. Activity tests were made on these catalysts by using the same equipment and reaction conditions as Example 1. The results thus obtained are as shown in Table-2.

TABLE-2

| | Catalyst | Additive (wt. %) | Specific surface area (m²/g) | Pore volume (cc/g) | Content of impurity (wt. %) | | | Conversion of ethanol (mole %) | Yield of ethylene (mole %) |
|---|---|---|---|---|---|---|---|---|---|
| | | | | | Na₂O | SO₃ | Fe₂O₃ | | |
| Comparative Example 4 | E | H₂SO₄ (1.1) | 155 | 0.36 | 0.04 | 0.90 | 0.002 | 95 | 75 |
| Comparative Example 5 | N631L | — | 420 | 0.48 | 0.02 | 0.10 | 0.07 | 96 | 75 |
| Comparative Example 6 | F | Fe₂O₃ (7.1) | 330 | 0.61 | 0.02 | 0.10 | 7.2 | 95 | 65 |

It is observed from Table-2 that the silica-alumina catalyst is superior in the conversion of ethanol, but is inferior by far in the yield of final product ethylene as compared with the alumina catalyst (Catalyst A) according to the present invention, whereby the former can not be qualified as the catalyst for use in the production of ethylene. It is also observed that Catalyst E obtained by adding H₂SO₄ to Catalyst A (alumina) and Catalyst F obtained by adding Fe₂O₃ to N631L (silica-alumina) respectively in order to clarify the influences of impurities on catalysts are both inferior in the yield of ethylene as compared with those free from impurities.

EXAMPLES 2 THROUGH 10

Various kinds of metal phosphates were added to Catalyst A of Example 1 in accordance to a kneading method (2 hours' kneading at room temperature). The resulting mixture was dried, pelleted and then calcined at 600° C. for 3 hours, thereby obtaining catalysts respectively. Activity tests were made on these catalysts by using the same equipment and reaction conditions as Example 1. The results thus obtained are as shown in Table-3.

It is observed from Table-3 that the addition of various kinds of phosphates to Catalyst A (alumina) can yield favorable results on improvements in not only the conversion of ethanol but also the yield of ethylene. MgHPO₄ or Mg₃(PO₄)₂ can, above all, be used effectively for that purpose. It is optimum that they are added in the proportions of 0.5 to 1.0 wt. % to the alumina. When added in the proportion of 7.0 wt. %, it brings about rapid deterioration of the activity of the catalyst. When the amounts of phosphates added are increased, the characteristics of the catalyst, namely specific surface area and pore volume, are observed to be substantially constant. While, however, only the mechanical strength increases with increasing contents of phosphates in the catalyst.

EXAMPLES 11 AND 12

Catalyst A according to Example 1 and Catalyst H according to Example 3 were employed respectively in an amount of 30 ml. These catalysts were subjected to the life test for the total period of 1500 hours under the same reaction conditions as Example 1 except that the liquid hourly space velocity of ethanol employed was

TABLE-3

| | Catalyst | Phosphate added (wt. %) | Specific surface area (m²/g) | Pore volume (cc/g) | Mechanical strength (Kg/pellet) | Conversion of ethanol (mole %) | Yield of ethylene (mole %) |
|---|---|---|---|---|---|---|---|
| Example 2 | G | MgHPO₄ (0.1) | 151 | 0.38 | 26.2 | 94 | 92 |
| Example 3 | H | (0.5) | 151 | 0.35 | 27.5 | 96 | 94 |
| Example 4 | I | (1.0) | 146 | 0.34 | 30.4 | 94 | 93 |
| Example 5 | J | (5.0) | 140 | 0.34 | 35.6 | 94 | 90 |
| Example 6 | K | Mg₃(PO₄)₂ (0.5) | 152 | 0.35 | 26.0 | 95 | 93 |
| Example 7 | L | CaHPO₄ (0.1) | 142 | 0.34 | 26.8 | 94 | 90 |
| Example 8 | M | (0.5) | 152 | 0.36 | 28.3 | 95 | 90 |
| Example 9 | N | (1.0) | 150 | 0.35 | 31.5 | 94 | 92 |
| Example 10 | O | ZnHPO₄ (0.5) | 151 | 0.33 | 26.9 | 94 | 92 |
| Comparative Example 7 | P | MgHPO₄ (7.0) | 135 | 0.30 | 38.4 | 80 | 75 |

Comparative Example 7

7.0 wt. % of MgHPO₄ was added to Catalyst A of Example 1 in accordance with the same procedure as employed in Examples 2 and 10 to obtain Catalyst P. Activity test was made on this catalyst according to the same procedure as Example 1. The obtained results are as shown in Table-3.

2.0 hour⁻¹. The results thus obtained are as shown in Table-4.

Comparative Example 8

Catalyst B (commercially available alumina) according to Comparative Example 1 was tested using the same procedure as employed in Example 11 through 12. The results thus obtained are as shown in Table-4.

TABLE-4

| | | Run duration | | | | | |
|---|---|---|---|---|---|---|---|
| | | 500 hrs | | 1000 hrs | | 1500 hrs | |
| | Catalyst | Conversion of ethanol (mole %) | Yield of ethylene (mole %) | Conversion of ethanol (mole %) | Yield of ethylene (mole %) | Conversion of ethanol (mole %) | Yield of ethylene (mole %) |
| Example 11 | A | 92 | 87 | 91 | 86 | 90 | 86 |
| Example 12 | H | 95 | 92 | 94 | 91 | 94 | 91 |
| Comparative Example 8 | B | 88 | 82 | 83 | 80 | 80 | 77 |

It can be seen from Table-4 that Catalyst A and Catalyst H according to the present invention are characterized by the fact that both their conversion of ethanol and yield of ethylene are subject to extremely little deterioration with the lapse of time as compared with the commercially available Catalyst B. Moreover, it is noted that Catalyst H having 0.5 wt. % of MgHPO$_4$ incorporated therein exhibits a higher catalytic stability for the production of ethylene as compared with Catalyst A. It will be apparent therefrom that the catalysts according to the present invention can exhibit extremely superior performances.

What is claimed is:

1. A catalyst which consists essentially of high purity activated alumina having a purity of at least 99.6 wt. % and containing not more than 0.05 wt. % of alkali metal, calculated as Na$_2$O, not more than 0.05 wt. % of sulfur, calculated as SO$_3$, not more than 0.05 wt. % of iron, calculated as Fe$_2$O$_3$, and not more than 0.05 wt. % of silicon, calculated as SiO$_2$, said high purity activated alumina having incorporated therein from 0.05 to 5 wt. %, based on the weight of said high purity activated alumina, of at least one phosphate of a metal selected from the group consisting of the metals of Group IIa, Group IIb, Group IIIa and Group IVb of the Periodic Table of the Elements.

2. A catalyst as claimed in claim 1 in which said metal is selected from the group consisting of the metals of Group IIa and IIb of the Periodic Table of the Elements.

3. A catalyst as claimed in claim 1 in which said metal is magnesium, calcium or zinc.

4. A catalyst as claimed in claim 1 in which said phosphate is MgHPO$_4$ or Mg$_3$(PO$_4$)$_2$.

5. A catalyst as claimed in claim 1 in which said phosphate is CaHPO$_4$.

6. A catalyst as claimed in claim 1 in which said phosphate is ZnHPO$_4$.

7. A catalyst as claimed in claim 1, claim 2, claim 3, claim 4, claim 5 or claim 6 in which the amount of said phosphate is from 0.1 to 1.0 wt. %, based on the weight of said high purity activated alumina.

8. A catalyst as claimed in claim 1 in which said high purity activated alumina has a specific surface area in the range of from 100 to 350 m$^2$/g and a pore volume in the range of from 0.15 to 0.50 cc/g.

* * * * *